(12) United States Patent
Kanaley et al.

(10) Patent No.: US 8,895,293 B2
(45) Date of Patent: Nov. 25, 2014

(54) ASSAY DEVICE HAVING UNIFORM FLOW AROUND CORNERS

(71) Applicant: Ortho-Clinical Diagnostics, Inc., Raritan, NJ (US)

(72) Inventors: James D. Kanaley, Honeoye Falls, NY (US); Zhong Ding, Pittsford, NY (US); Philip C. Hosimer, Rochester, NY (US); Edward R. Scalice, Penfield, NY (US); Susan Danielson, Honeoye Falls, NY (US); David A. Tomasso, Rochester, NY (US); Timothy C. Warren, Rochester, NY (US)

(73) Assignee: Ortho-Clinical Diagnostics, Inc., Raritan, NJ (US)

( * ) Notice: Subject to any disclaimer, the term of this patent is extended or adjusted under 35 U.S.C. 154(b) by 0 days.

(21) Appl. No.: 13/744,451

(22) Filed: Jan. 18, 2013

(65) Prior Publication Data

US 2013/0189796 A1    Jul. 25, 2013

Related U.S. Application Data

(60) Provisional application No. 61/588,745, filed on Jan. 20, 2012.

(51) Int. Cl.
*B01L 3/00* (2006.01)
*G01N 1/28* (2006.01)
*G01N 33/543* (2006.01)

(52) U.S. Cl.
CPC ............. *G01N 1/28* (2013.01); *B01L 2400/086* (2013.01); *G01N 33/54366* (2013.01); *B01L 3/502746* (2013.01)
USPC ............ 435/287.1; 422/502; 422/507; 435/4; 435/286.5; 436/518

(58) Field of Classification Search
None
See application file for complete search history.

(56) References Cited

U.S. PATENT DOCUMENTS

| 5,120,643 A | 6/1992 | Ching et al. |
| 5,559,041 A | 9/1996 | Kang et al. |

(Continued)

FOREIGN PATENT DOCUMENTS

| WO | WO 03103835 A1 | 12/2003 |
| WO | WO 2005089082 A3 | 11/2005 |

(Continued)

OTHER PUBLICATIONS

U.S. Appl. No. 13/744,617, Kanaley et al.

*Primary Examiner* — Melanie Y Brown
*Assistant Examiner* — Rebecca Martinez
(74) *Attorney, Agent, or Firm* — Todd J. Burns

(57) ABSTRACT

An assay device includes: a liquid sample zone; a reagent zone downstream and in fluid communication with the sample zone containing a reagent material; a detection zone in fluid communication with the reagent zone having capture elements bound thereto; and a wicking zone in fluid communication with the capture zone having a capacity to receive liquid sample flowing from the detection zone. The sample receiving zone, the reagent zone, the detection zone and the wicking zone define a fluid flow path and at least a part of the fluid flow path has a substrate and projections which extend substantially vertically from the substrate, wherein the projections have a height, cross-section and a distance between one another that defines a space between the projections capable of generating capillary flow parallel to the substrate surface. In addition, the fluid flow path having projections includes a corner section which changes the direction of the flow path. The projections in or around the corner section are modified to maintain the configuration of the flow front of the sample flowing through the flow path after the corner is substantially the same configuration as before the corner.

14 Claims, 12 Drawing Sheets

(56) References Cited

U.S. PATENT DOCUMENTS

| | | | |
|---|---|---|---|
| 5,714,389 A | 2/1998 | Charlton et al. | |
| 5,842,787 A * | 12/1998 | Kopf-Sill et al. | 366/340 |
| 6,139,800 A | 10/2000 | Chandler | |
| 6,228,660 B1 | 5/2001 | May et al. | |
| 6,270,641 B1 | 8/2001 | Griffiths et al. | |
| 6,372,542 B1 | 4/2002 | Martin et al. | |
| 6,451,264 B1 | 9/2002 | Bhullar et al. | |
| 6,669,907 B1 | 12/2003 | Buechler | |
| 6,733,682 B1 | 5/2004 | Björkman et al. | |
| 6,811,736 B1 | 11/2004 | Ohman et al. | |
| 6,884,370 B2 | 4/2005 | Öhman et al. | |
| 7,005,301 B2 * | 2/2006 | Cummings et al. | 436/180 |
| 7,416,700 B2 | 8/2008 | Buechler et al. | |
| 7,524,464 B2 | 4/2009 | Ahn et al. | |
| 7,695,687 B2 | 4/2010 | Delamarche et al. | |
| 2003/0152927 A1 | 8/2003 | Jakobsen et al. | |
| 2004/0077103 A1 | 4/2004 | Buechler | |
| 2004/0129678 A1 | 7/2004 | Crowley | |
| 2004/0259076 A1 | 12/2004 | Farrow | |
| 2005/0042766 A1 | 2/2005 | Ohman et al. | |
| 2006/0239859 A1 | 10/2006 | Ohman et al. | |
| 2006/0285996 A1 | 12/2006 | Ohman et al. | |
| 2006/0289787 A1 | 12/2006 | Ohman et al. | |
| 2007/0122819 A1 | 5/2007 | Wu et al. | |
| 2007/0231883 A1 | 10/2007 | Lindstrom et al. | |
| 2009/0123336 A1 | 5/2009 | Yang et al. | |
| 2009/0130658 A1 | 5/2009 | Barlag et al. | |
| 2010/0009430 A1 * | 1/2010 | Wan et al. | 435/287.1 |
| 2010/0166611 A1 | 7/2010 | Desmet | |
| 2010/0167318 A1 | 7/2010 | Linder | |
| 2010/0248394 A1 * | 9/2010 | Ohman et al. | 436/518 |
| 2013/0189672 A1 | 7/2013 | Ding | |
| 2013/0189673 A1 | 7/2013 | Scalice et al. | |
| 2013/0210036 A1 | 8/2013 | Kanaley et al. | |

FOREIGN PATENT DOCUMENTS

| | | |
|---|---|---|
| WO | WO 2005118139 A1 | 12/2005 |
| WO | WO 2006137785 A1 | 12/2006 |
| WO | WO 2007149042 A1 | 12/2007 |
| WO | WO 2013/109821 A1 | 7/2013 |

* cited by examiner

ASSAY DEVICE HAVING UNIFORM FLOW AROUND CORNERS

CROSS REFERENCE TO RELATED APPLICATIONS

This patent application claims priority to U.S. Provisional Application No. 61/588,745, filed Jan. 20, 2012, the disclosure of which is incorporated by reference in its entirety.

FIELD OF THE INVENTION

The present invention relates to the field of diagnostic assays, and in particular to lateral flow assays where an analyte to be detected is present in a biological or non-biological sample.

BACKGROUND

Diagnostic assays are widespread and central for the diagnosis, treatment and management of many diseases. Different types of diagnostic assays have been developed over the years in order to simplify the detection of various analytes in clinical samples such as blood, serum, plasma, urine, saliva, tissue biopsies, stool, sputum, skin or throat swabs and tissue samples or processed tissue samples. These assays are frequently expected to give a fast and reliable result, while being easy to use and inexpensive to manufacture. Understandably it is difficult to meet all these requirements in one and the same assay. In practice, many assays are limited by their speed. Another important parameter is sensitivity. Recent developments in assay technology have led to increasingly more sensitive tests that allow detection of an analyte in trace quantities as well the detection of disease indicators in a sample at the earliest time possible.

A common type of disposable assay device includes a zone or area for receiving the liquid sample, a conjugate zone also known as a reagent zone, and a reaction zone also known as a detection zone. These assay devices are commonly known as lateral flow test strips. They employ a porous material, e.g., nitrocellulose, defining a path for fluid flow capable of supporting capillary flow. Examples include those shown in U.S. Pat. Nos. 5,559,041, 5,714,389, 5,120,643, and 6,228,660 all of which are incorporated herein by reference in their entireties.

The sample-addition zone frequently consists of a more porous material, capable of absorbing the sample, and, when separation of blood cells is desired, also effective to trap the red blood cells. Examples of such materials are fibrous materials, such as paper, fleece, gel or tissue, comprising e.g. cellulose, wool, glass fiber, asbestos, synthetic fibers, polymers, or mixtures of the same.

Another type of assay device is a non-porous assay having projections to induce capillary flow. Examples of such assay devices include the open lateral flow device as disclosed in WO 2003/103835, WO 2005/089082, WO 2005/118139, and WO 2006/137785, all of which are incorporated herein by reference in their entireties.

A known non-porous assay device is shown in FIG. 1. The assay device 1, has at least one sample addition zone 2, a reagent zone 3, at least one detection zone 4, and at least one wicking zone 5. The zones form a flow path by which sample flows from the sample addition zone to the wicking zone. Also included are capture elements, such as antibodies, in the detection zone 4, capable of binding to the analyte, optionally deposited on the device (such as by coating); and a labeled conjugate material also capable of participating in reactions that will enable determination of the concentration of the analyte, deposited on the device in the reagent zone, wherein the labeled conjugate material carries a label for detection in the detection zone. The conjugate material is dissolved as the sample flows through the reagent zone forming a conjugate plume of dissolved labeled conjugate material and sample that flows downstream to the detection zone. As the conjugate plume flows into the detection zone, the conjugated material will be captured by the capture elements such as via a complex of conjugated material and analyte (as in a "sandwich" assay) or directly (as in a "competitive" assay). Unbound dissolved conjugate material will be swept past the detection zone into the at least one wicking zone 5.

An instrument such as that disclosed US 20060289787A1, US20070231883A1, U.S. Pat. No. 7,416,700 and U.S. Pat. No. 6,139,800 all incorporated by reference in their entireties, is able to detect the bound conjugated material in the detection zone. Common labels include fluorescent dyes that can be detected by instruments which excite the fluorescent dyes and incorporate a detector capable of detecting the fluorescent dyes.

The sample size for such typical assay devices as shown in FIG. 1 are generally on the order of 200 µl. Such a sample size requires a venous blood draw from a medical professional such as a phlebotomist. There is an increasing need for lateral flow devices that are able to function with a much smaller sample size to accommodate the amount of blood available from a so-called "fingerstick" blood draw, which is on the order of 25 µl or less. Such a small amount of sample is the amount of blood in a drop of blood after pricking a finger tip with a lancet. Home blood glucose meters typically use a drop of blood obtained in such a fashion to provide glucose levels in blood. Such a smaller sample size would not require a medical professional to draw the blood and would provide greater comfort to the patients providing the sample for analysis.

To reduce the sample size required, the dimensions of the lateral flow assay devices are reduced to accommodate the smaller sample size. However, it has been found that reducing the sample size and dimensions of the device provides inadequate conjugate in the detection zone and accordingly less signal that can be read by the instrument. The inadequate conjugate in the detection zone is believed to be due to reduced sample size and inefficient use of the sample in the device, amongst other conditions. Another drawback of reducing dimensions is that the width of the detection zone will also be reduced, again making less signal available that can be read by the instrument.

Another disadvantage with a typical assay design shown in FIG. 1 is that the length of the detection zone is very short and can only measure one analyte and cannot measure additional analytes or controls (e.g., internal positive and negative controls). While it is possible to increase the length of the detection zone along a straight line, this leads to an assay device that is larger than desired for point-of-care applications, has increased use of materials, and is more expensive to manufacture.

To gain the advantages of a longer detection zone in a smaller foot print, the detection zone can be lengthened by bending or folding the flow path of the detection zone or other part of the flow path around one or more corners to create a serpentine design that can be contained within a smaller foot print. U.S. Pat. No./Publication Nos. U.S. Pat. No. 7,524,464, 2010/0167318, 2009/0130658, 2009/0123336 all disclose fluidic devices having folded or serpentine flow paths.

The present inventors found, however, that placing turns or corners in the flow path of an assay device that uses micropillars or projections, will not provide satisfactory results. This is believed due to a flow rate that is slower in the outer edge of the channel (longer flow path) than the flow rate in the inner edge (shorter flow path) around the turn or corner. This leads to a reagent plume coming from the reagent zone that does not adequately spread across as much of the width of the detection zone as possible, which in turn leads to a decreased signal that can be read by the instrument reading the signal. The problems of a reagent plume not covering as much of the detection zone as possible is a particular problem in smaller devices that have narrower detection zones. In other words, it is important for the reagent plume to spread across as much of the width of the detection zone as possible to provide the maximum amount of signal to be read by the read window of the instrument. Another problem for the biased flow is that wash efficiency is poor since part of the plume near the outer edge of the turn takes much longer to get washed out due to its slower flow rate relative to the inner edge.

Accordingly, there is a need for an assay device that can provide a longer detection zone in a small footprint while maintaining desired flow characteristics of the conjugated sample through the detection zone.

SUMMARY OF THE INVENTION

The present invention is directed to an assay device that alleviates one or more the foregoing problems described above.

One aspect of the invention is directed to an assay device, which includes: a liquid sample zone; a reagent zone downstream and in fluid communication with the sample zone containing a reagent material; a detection zone in fluid communication with the reagent zone having capture elements bound thereto; and a wicking zone in fluid communication with the capture zone having a capacity to receive liquid sample flowing from the detection zone The sample receiving zone, the reagent zone, the detection zone and the wicking zone define a fluid flow path and at least a part of the fluid flow path has a substrate and projections which extend substantially vertically from the substrate. The projections have a height, cross-section and a distance between one another that defines a space between the projections capable of generating capillary flow parallel to the substrate surface. The fluid flow path having projections includes a corner section which changes the direction of the flow path. The projections in or around the corner section are modified to maintain the configuration of the flow front of the sample flowing through the flow path after the corner is substantially the same configuration as before the corner.

According to another aspect of the invention, there has been provided a method for performing an assay on a liquid sample for the detection of one or more analytes of interest. The method includes: providing a liquid sample zone; providing a reagent zone downstream and in fluid communication with the sample addition zone containing a reagent material; providing a detection zone in fluid communication with the reagent zone; providing a wicking zone in fluid communication with the detection zone having a capacity to receive liquid sample flowing from the detection zone. The sample receiving zone, the reagent zone, the detection zone and the wicking zone define a fluid flow path and at least a part of the fluid flow path has a substrate and projections which extend substantially vertically from the substrate. The projections have a height, cross-section and a distance between one another that defines a space between the projections capable of generating capillary flow parallel to the substrate surface. The at least part of the fluid flow path having projections has a corner section to change the direction of the flow path, wherein the projections in or around the corner section are modified to maintain the flow front of the sample flowing through the flow path after the corner is substantially the same configuration as before the corner. A liquid sample containing the analyte(s) of interest is deposited onto the sample zone; the sample is moved by capillary action into the reagent zone where it dissolves the reagent material; the sample flows away from the reagent zone having a dissolved reagent plume and into a detection zone by capillary action, where the analytes are detection by reading a signal that is generated to determine the presence or concentration of the analyte(s); and the sample and any other unbound material flows into the wicking zone.

According to still another aspect of the invention, there has been provided a method of controlling the flow of a liquid around the corner section of a fluid flow path in an assay device that includes: providing a liquid sample zone; providing a reagent zone downstream and in fluid communication with the sample addition zone containing a reagent material; providing a detection zone in fluid communication with the reagent zone; providing a wicking zone in fluid communication with the detection zone having a capacity to receive liquid sample flowing from the detection zone, wherein the sample receiving zone, the reagent zone, the detection zone and the wicking zone define a fluid flow path and at least a part of the fluid flow path has a substrate and projections which extend substantially vertically from the substrate, wherein the projections have a height, cross-section and a distance between one another that defines a space between the projections capable of generating capillary flow parallel to the substrate surface, and wherein the at least part of the fluid flow path having projections has a corner section to change the direction of the flow path, wherein the projections in or around the corner section are modified to maintain the flow front of the sample flowing through the flow path after the corner is substantially the same configuration as before the corner; adding sample to the sample addition zone; flowing the sample from the sample addition through the reagent zone into and through the detection zone and into the wicking zone, wherein the sample encounters at least one corner section, anywhere in the flow path and wherein the modifications to the projections maintain the configuration of the flow front of the sample before and after the corner.

Further objects, features and advantages of the present invention will be apparent to those skilled in the art from detailed consideration of the preferred embodiments that follow.

DETAILED DESCRIPTION OF PREFERRED EMBODIMENTS

Figure 1:
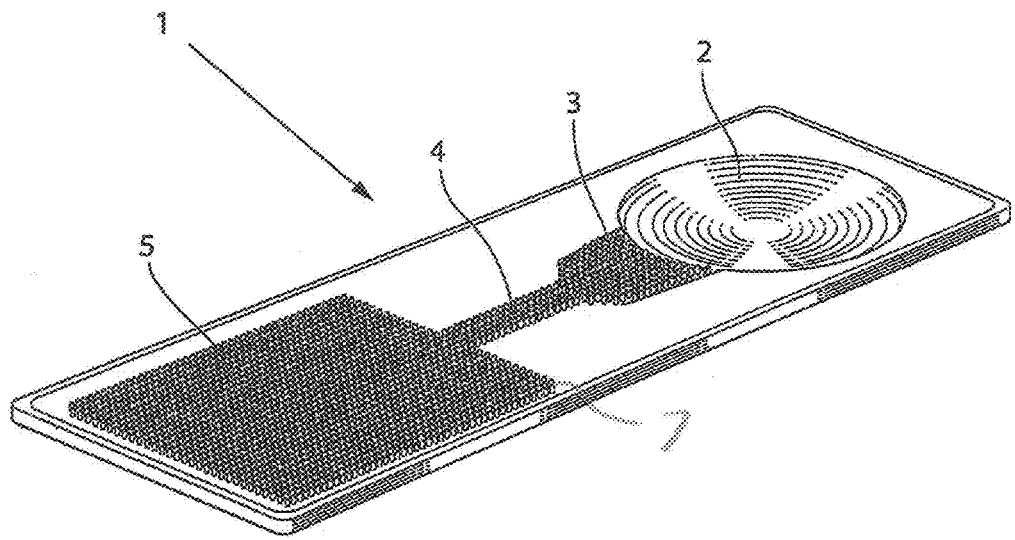
FIG. 1 shows a known assay device.

As used in this specification and the appended claims, the singular forms "a", "an" and "the" include plural referents unless the context clearly dictates otherwise.

The term "about" as used in connection with a numerical value throughout the description and the claims denotes an interval of accuracy, familiar and acceptable to a person skilled in the art. The interval is preferably ±10%.

The term "sample" herein means a volume of a liquid, solution or suspension, intended to be subjected to qualitative or quantitative determination of any of its properties, such as the presence or absence of a component, the concentration of a component, etc. Typical samples in the context of the present invention are human or animal bodily fluids such as blood, plasma, serum, lymph, urine, saliva, semen, amniotic fluid, gastric fluid, phlegm, sputum, mucus, tears, stool, etc. Other types of samples are derived from human or animal tissue samples where the tissue sample has been processed into a liquid, solution, or suspension to reveal particular tissue components for examination. The embodiments of the present invention are applicable to all bodily samples, but preferably to samples of whole blood, urine or sputum.

In other instances, the sample can be related to food testing, environmental testing, bio-threat or bio-hazard testing, etc. This is only a small example of samples that can be used in the present invention.

In the present invention, the determination based on lateral flow of a sample and the interaction of components present in the sample with reagents present in the device or added to the device during the procedure and detection of such interaction, either qualitatively or quantitatively, may be for any purpose, such as diagnostic purposes. Such tests are often referred to as lateral flow assays.

Examples of diagnostic determinations include, but are not limited to, the determination of analytes, also called markers, specific for different disorders, e.g. chronic metabolic disorders, such as blood glucose, blood ketones, urine glucose (diabetes), blood cholesterol (atherosclerosis, obesity, etc); markers of other specific diseases, e.g. acute diseases, such as coronary infarct markers (e.g. troponin-T, NT-ProBNP), markers of thyroid function (e.g. determination of thyroid stimulating hormone (TSH)), markers of viral infections (the use of lateral flow immunoassays for the detection of specific viral antibodies); etc.

Yet another important field is the field of companion diagnostics where a therapeutic agent, such as a drug, is administered to an individual in need of such a drug. An appropriate assay is then conducted to determine the level of an appropriate marker to determine whether the drug is having its desired effect. Alternatively, the assay device of the present invention can be used prior to administration of a therapeutic agent to determine if the agent will help the individual in need.

Yet another important field is that of drug tests, for easy and rapid detection of drugs and drug metabolites indicating drug abuse; such as the determination of specific drugs and drug metabolites (e.g. THC) in urine samples etc.

The term "analyte" is used as a synonym of the term "marker" and intended to encompass any chemical or biological substance that is measured quantitatively or qualitatively and can include small molecules, proteins, antibodies, DNA, RNA, nucleic acids, virus components or intact viruses, bacteria components or intact bacteria, cellular components or intact cells and complexes and derivatives thereof.

The terms "zone", "area" and "site" are used in the context of this description, examples and claims to define parts of the fluid flow path on a substrate, either in prior art devices or in a device according to an embodiment of the invention.

The term "reaction" is used to define any reaction, which takes place between components of a sample and at least one reagent or reagents on or in the substrate, or between two or more components present in the sample. The term "reaction" is in particular used to define the reaction, taking place between an analyte and a reagent as part of the qualitative or quantitative determination of the analyte.

The term "substrate" means the carrier or matrix to which a sample is added, and on or in which the determination is performed, or where the reaction between analyte and reagent takes place.

Figure 2:
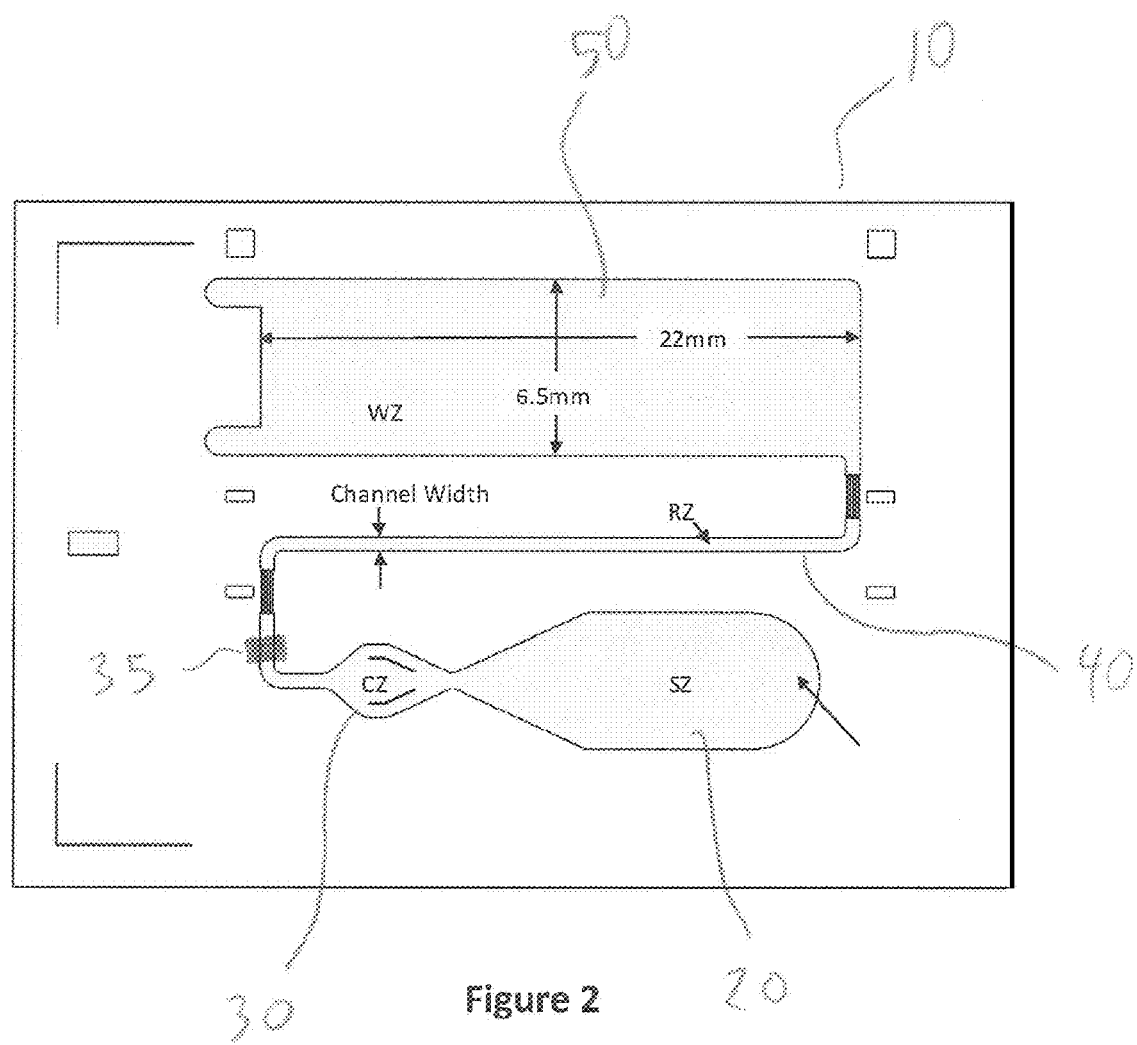
FIG. 2 shows a schematic view of an assay device having corners in the fluid flow path according to an embodiment of the invention.
Figure 3:
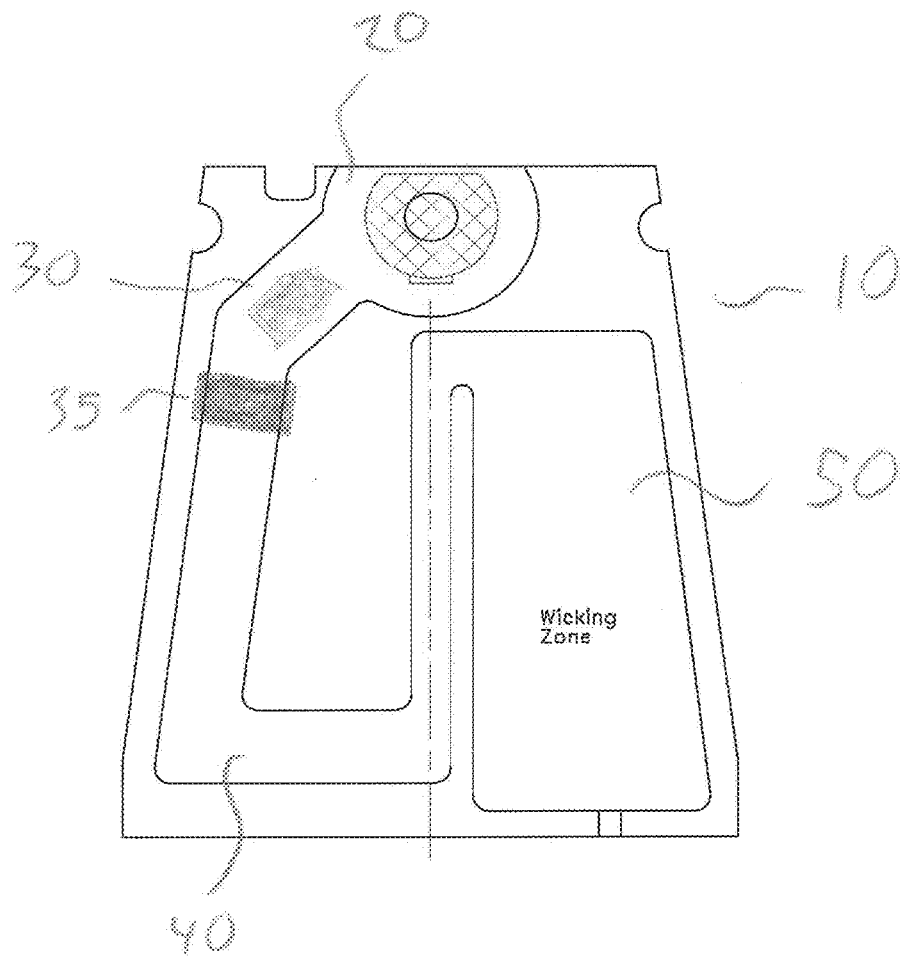
FIG. 3 shows a schematic view of an assay device having corners in the flow path according to another embodiment of the invention.

The present invention is directed to a lateral flow assay device for determining the presence or amount of at least one analyte that solves, at least in part, the problem of lowered signal due to a narrow reagent plume (described below) or reduced sample size. FIGS. 2 and 3 show a schematic view of a preferred embodiment of such a device according to the invention. The assay device 10, has at least one sample zone 20, at least one reagent zone 30, at least one detection zone 40, and at least one wicking zone 50. The zones form a flow path by which sample flows from the sample zone to the wicking zone.

Components of the assay device (i.e., a physical structure of the device whether or not a discrete piece from other parts of the device) can be prepared from copolymers, blends, laminates, metallized foils, metallized films or metals. Alternatively, device components can be prepared from copolymers, blends, laminates, metallized foils, metallized films or metals deposited one of the following materials: polyolefins, polyesters, styrene containing polymers, polycarbonate, acrylic polymers, chlorine containing polymers, acetal homopolymers and copolymers, cellulosics and their esters, cellulose nitrate, fluorine containing polymers, polyamides, polyimides, polymethylmethacrylates, sulfur containing polymers, polyurethanes, silicon containing polymers, glass, and ceramic materials. Alternatively, components of the device are made with a plastic, elastomer, latex, silicon chip, or metal; the elastomer can comprise polyethylene, polypropylene, polystyrene, polyacrylates, silicon elastomers, or latex. Alternatively, components of the device can be prepared from latex, polystyrene latex or hydrophobic polymers; the hydrophobic polymer can comprise polypropylene, polyethylene, or polyester. Alternatively, components of the device can comprise TEFLON®, polystyrene, polyacrylate, or polycarbonate. Alternatively, device components are made from plastics which are capable of being embossed, milled or injection molded or from surfaces of copper, silver and gold films upon which may be adsorbed various long chain alkanethiols. The structures of plastic which are capable of being milled or injection molded can comprise a polystyrene, a polycarbonate, or a polyacrylate. In a particularly preferred embodiment, the assay device is injection molded from a cyclo olefin polymer, such as those sold under the name Zeonor®. Preferred injection molding techniques are described in U.S. Pat. Nos. 6,372,542, 6,733,682, 6,811,736, 6,884,370, and 6,733,682, all of which are incorporated herein by reference in their entireties.

The flow path can include open or closed paths, grooves, and capillaries. Preferably the flow path comprises a lateral flow path of adjacent projections, having a size, shape and mutual spacing such that capillary flow is sustained through the flow path. In one embodiment, the flow path is in a channel within the substrate having a bottom surface and side walls. In this embodiment, the projections protrude from the bottom surface of the channel. The side walls may or may not contribute to the capillary action of the liquid. If the sidewalls do not contribute to the capillary action of the liquid, then a gap can be provided between the outermost projections and the sidewalls to keep the liquid contained in the flow path defined by the projections. FIG. 1 shows projections 7.

In one embodiment the flow path is at least partially open. In another embodiment the flow path is entirely open. Open means that there is no lid or cover at a capillary distance. Thus the lid, if present as a physical protection for the flow path, does not contribute to the capillary flow in the flow path. An open lateral flow path is described for example in the following published applications: WO 2003/103835, WO 2005/089082; WO 2005/118139; WO 2006/137785; and WO 2007/149042, all of which are incorporated by reference in their entireties. The projections have a height (H), diameter (D) and a distance or distances between the projections (t1, t2) such, that lateral capillary flow of the fluid, such as plasma, preferably human plasma, in the zone is achieved. These dimensions are shown in US 2006/0285996, which is incorporated by reference in its entirety. In addition to optimizing the above-mentioned height, diameter and a distance or distances between the projections, the projections may be given a desired chemical, biological or physical functionality, e.g. by modifying the surface of the projections. In one embodiment, the projections have a height in the interval of about 15 to about 150 µm, preferably about 30 to about 100 µm, a diameter of about 10 to about 160 µm, preferably 40 to about 100 µm, and a gap or gaps between the projections of about 3 to about 200 µm, preferably 10 to about 100 µm or 5 to 50 µm from each other. The flow channel may have a length of about 5 to about 500 mm, preferably about 10 to about 100 mm, and a width of about 0.3 to about 10 mm, preferably about 0.3 to about 3 mm, preferably about 0.5 to 1.5, and preferably about 0.5 to 1.2 mm.

While most detection will occur in the detection zone portion of the fluid flow path, it is also possible that detection may occur in other parts of the device. For example, non-invasive, non-reactive sample integrity measurements may occur between the sample zone and the reagent zone or reagent addition zone, preferably after a filter element, if present. Other measurements may include blanks reads, one part of a two part reaction sequence as for measuring both hemoglobin and glycated hemoglobin for determination of HbA1c, etc.

The liquid sample zone 20, also referred to as the liquid sample addition zone, receives sample from a sample dispenser, such as a pipette. The sample is typically deposited onto the top of the zone. The sample addition zone is capable of transporting the liquid sample from the point where the sample is deposited to the reagent zone, through an optional filter and reagent addition zone, preferably through capillary flow. The capillary flow inducing structure can include porous materials, such as nitrocellulose, or preferably through projections, such as micro-pillars, as shown in FIG. 1. In those devices that can use finger stick volumes of blood, the sample can be directly touched off from the finger, or by a capillary pipette.

A filter material (not shown) can be placed in the sample addition zone to filter particulates from the sample or to filter blood cells from blood so that plasma can travel further through the device.

Located between the sample addition zone and the detection zone is a reagent zone 30. The reagent zone can include reagent(s) integrated into the analytical element and are generally reagents useful in the reaction—binding partners such as antibodies or antigens for immunoassays, substrates for enzyme assays, probes for molecular diagnostic assays, or are auxiliary materials such as materials that stabilize the integrated reagents, materials that suppress interfering reactions, etc. Generally one of the reagents useful in the reaction bears a detectable signal as discussed below. In some cases the reagents may react with the analyte directly or through a cascade of reactions to form a detectable signal such as, but not restricted to, a molecule detectable using spectroscopy such as a colored or fluorescent molecule. The amount of reagent in the reagent zone can be adjusted by the length of reagent deposited into the device while maintaining the same reagent width. The amount of reagent can also be adjusted by changing the width while maintaining the length. The amount of reagent can further be adjusted by changing both width and length simultaneously. In one preferred embodiment, the reagent zone includes conjugate material. The term conjugate means any moiety bearing both a detection element and a binding partner.

The detection element is an agent which is detectable with respect to its physical distribution or/and the intensity of the signal it delivers, such as but not limited to luminescent molecules (e.g. fluorescent agents, phosphorescent agents, chemiluminescent agents, bioluminescent agents and the like), colored molecules, molecules producing colors upon reaction, enzymes, radioisotopes, ligands exhibiting specific binding and the like. The detection element also referred to as a label is preferably chosen from chromophores, fluorophores, radioactive labels, and enzymes. Suitable labels are available from commercial suppliers, providing a wide range of dyes for the labeling of antibodies, proteins, and nucleic acids. There are, for example, fluorophores spanning practically the entire visible and infrared spectrum. Suitable fluorescent or phosphorescent labels include for instance, but are not limited to, fluoresceins, Cy3, Cy5 and the like. Suitable chemoluminescent labels are for instance but are not limited to luminol, cyalume and the like.

Similarly, radioactive labels are commercially available, or detection elements can be synthesized so that they incorporate a radioactive label. Suitable radioactive labels are for instance but are not limited to radioactive iodine and phosphorus; e.g. $^{125}I$ and $^{32}P$.

Suitable enzymatic labels are, for instance, but are not limited to, horseradish peroxidase, beta-galactosidase, luciferase, alkaline phosphatase and the like. Two labels are "distinguishable" when they can be individually detected and preferably quantified simultaneously, without significantly disturbing, interfering or quenching each other. Two or more labels may be used, for example, when multiple analytes or markers are being detected.

The binding partner is a material that can form a complex that can be used to determine the presence of or amount of an analyte. For example, in an "sandwich" assay, the binding partner in the conjugate can form a complex including the analyte and the conjugate and that complex can further bind to another binding partner, also called a capture element, integrated into the detection zone. In a competitive immunoassay, the analyte will interfere with binding of the binding partner in the conjugate to another binding partner, also called a capture element, integrated into the detection zone. Example binding partners included in conjugates include antibodies, antigens, analyte or analyte-mimics, protein, etc.

Optionally located in the fluid flow path, before or after the reagent zone and before the detection zone is a reagent addition zone. The reagent addition zone is shown as 35 in FIGS. 2 and 3. The reagent addition zone can allow addition of a reagent externally from the device. For example, the reagent addition zone may be used to add an interrupting reagent that may be used to wash the sample and other unbound components present in the fluid flow path into the wicking zone. In a preferred embodiment the reagent addition zone 35 is located after the reagent zone 30.

Downstream from the liquid sample zone and the reagent zone is the detection zone 40 which is in fluid communication with the sample addition zone. The detection zone 40 may include projections such as those described above. As also noted above, these projections are preferably integrally molded into the substrate from an optical plastic material such as Zeonor, such as injection molding or embossing. The width of the flow channel in the detection zone is typically on the order of 2 mm for conventional size devices, however, some lower volume devices, such as those described above and in copending application entitled "Lower Volume Assay Device Having Increased Sensitivity" (Application No. 61/588,758, first named inventor: Phil Hosimer) filed Jan. 20, 2012 and incorporated by reference in its entirety, are significantly narrower, e.g., 1.5 mm or less.

The detection zone is where any detectable signal is read. In a preferred embodiment attached to the projections in the detection zone are capture elements. The capture elements can include binding partners for the conjugate or complexes containing the conjugate, as described above. For example, if the analyte is a specific protein, the conjugate may be an antibody that will specifically bind that protein coupled to a detection element such as a fluorescence probe. The capture element could then be another antibody that also specifically binds to that protein. In another example, if the marker or analyte is DNA, the capture molecule can be, but is not limited to, synthetic oligonucleotides, analogues thereof, or specific antibodies. Other suitable capture elements include antibodies, antibody fragments, aptamers, and nucleic acid sequences, specific for the analyte to be detected. A non-limiting example of a suitable capture element is a molecule that bears avidin functionality that would bind to a conjugate containing a biotin functionality. The detection zone can include multiple detection zones. The multiple detection zones can be used for assays that include one or more markers. In the event of multiple detection zones, the capture elements can include multiple capture elements, such as first and second capture elements. The conjugate can be pre-deposited on the assay device, such as by coating in the reagent zone. Similarly the capture elements can be pre-deposited on the assay device on the detection zone. Preferably, both the detection and capture elements are pre-deposited on the assay device, on the reaction zone and detection zone, respectively.

After the sample has been delivered to the sample zone, it will encounter the reagent zone. After the sample has flowed through and interacted with the reagent zone and optionally the reagent addition zone, the sample and a reagent plume will be contained in the fluid flow. The reagent plume can contain any of the reagent materials that have been dissolved in the reaction zone or those added through the reagent addition zone. The reagent plume can include the conjugate having both the detection element and binding partner, in which case it is often referred to as a conjugate plume. As noted throughout, one challenge facing the inventors was to keep the reagent plume as wide as possible as it enters the detection zone. The reagent zone can include multiple reagent cells such as described in copending application "Assay Device Having Multiple Reagent Cells" (Ser. No. 61/588,738, first named inventor Zhong Ding) filed Jan. 20, 2010 and incorporated by reference in its entirety, in which case multiple reagent plumes will exit the reagent zone to recombine partially or completely downstream.

The present invention is based, in part, on the surprising discovery that in a device, where it may be possible to design a flow path to include corners to reduce the size and foot print of the device, simply fabricating corners or turns in the device, without more, will result in an assay device that has less signal that can be read by the detection instrument and poorer wash efficiency, and hence will result in assays having lower sensitivity. After further investigation by the inventors, it was discovered that going around corners using projections, such as those described herein, having the same pattern as the straight sections of the detection zone will adversely affect the configuration of the flow front that is present as a sample progresses down the flow path of the assay device. In other words, the configuration of the flow front after the corner section will be different from the configuration of the flow front before the corner section. In the present invention, a uniform flow front is the preferred flow. A uniform flow front is the flow of the fluid, such as plasma, in the flow path, where the front edge of the fluid is substantially perpendicular to the direction of fluid flow.

Figure 4:
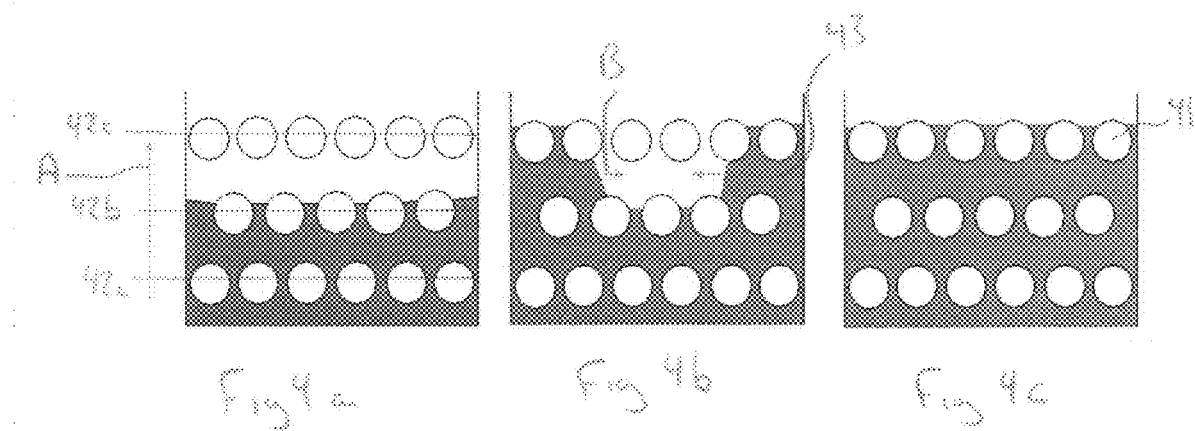
FIGS. 4a-c shows enlarged schematic views of micropillars in a flow path and the fluid wetting characteristics of the sample in the flow path.

More specifically, the wetting of the flow path as observed from above is shown in FIGS. 4a-c. The direction of fluid flow is shown by arrow A in FIG. 4a. While the description of fluid interaction with the flow path is described in connection with fluid wetting (i.e., the initial flow of liquid through the device), the description and advantages of the invention described herein is equally, if not more, applicable to steady state flow through the device after wetting. The rows of pillars or projections 41 are shown as reference numbers 42a-42c. In the device of the present invention, the projections or pillars 41 are patterned so that as the sample fluid advances from one row to the next, wetting occurs in a repeatable pattern by first wetting all pillars within a row. Once the pillars in a row are wetted and the front of the fluid is substantially perpendicular to the flow direction, the fluid advances to the outside edges of the next row, such as shown in FIG. 4b, where the fluid advances from row 42b to 42c along the outside edges 43, where the fluid will then wet the projections within row 42c as shown by arrow B, before advancing to the next row (not shown) along the outside edges. This ensures that the projections are uniformly wetted row by row and the flow front of the fluid is across the entire width of the flow path and is substantially perpendicular to the direction of fluid flow, i.e., a uniform flow front. Uniform flow across the entire width of the detection zone is important because the reagent plume containing the readable label or signal reagent that exits the reagent zone should cover as much of the width of the flow path as possible, such that the read window of the detection instrument, which is typically on the order of 1 mm, will read as much signal as possible, which is made possible by the reagent plume extending the entire width of the detection zone. As noted above, a wide reagent plume relative to the detection zone width is particularly important in smaller assay devices where the width of the detection zone may be narrower.

However the inventors have found that in those devices having regions where the flow path is required to turn corners, uniform flow across the width of the flow path is not achieved. In other words, if the pillars 41 follow the same orientation throughout the whole channel length, flow may not follow the uniform fill pattern that is desired and shown in FIG. 4.

Figure 5:
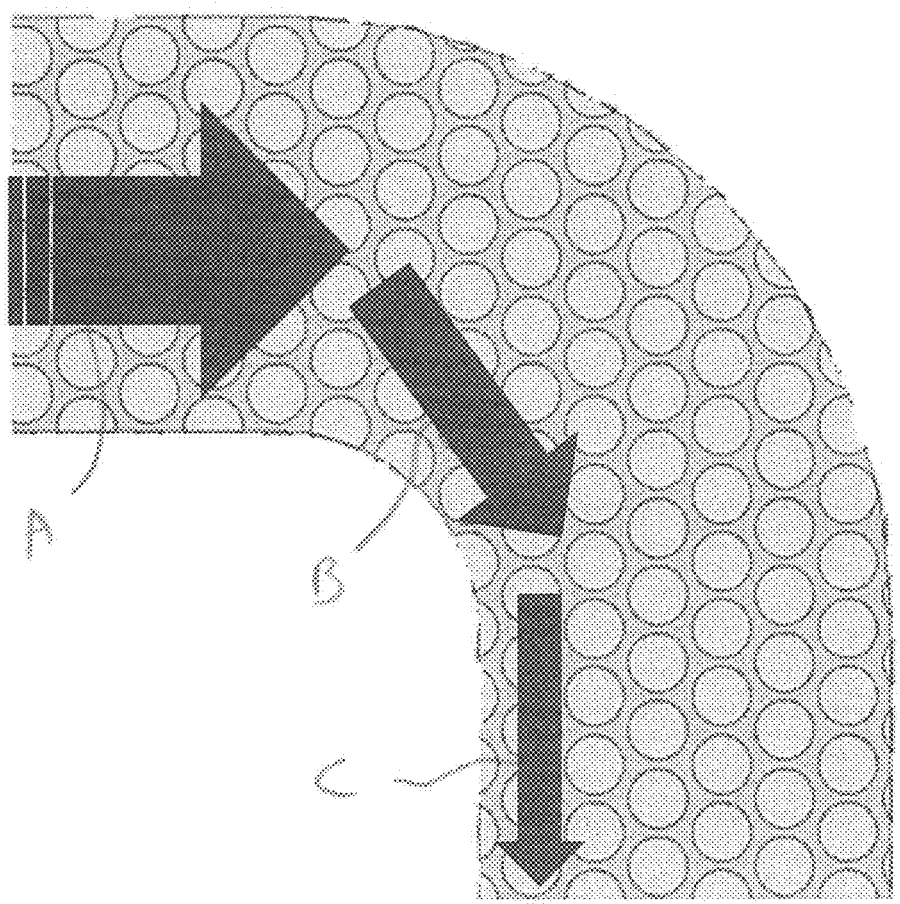
FIG. 5 shows an enlarged schematic view of a corner of a flow path in a detection zone without any correction to compensate for irregular wetting.

More specifically, if the alignment or pattern of the projections remains the same around the corner and lengthwise in the subsequent flow path, the fluid as it is flowing around the corner will be skewed toward the inside edges of the corner and associated inner flow path edge as shown by the arrows A-C in FIG. 5. As shown in more detail in FIG. 5 as the fluid flow front moves toward the corner from the upstream flow path it covers the width of the flow path as shown by the wide arrow A. As the flow enters the corner or turn, the flow begins to narrow and move toward the inside of the turn as shown by narrower arrow B. As the flow comes out of the turn, the flow is initially biased along the inside edge of the flow path as shown by arrow C. Such a narrow wetting pattern is generally an undesirable wetting pattern for flow paths because of the need for the reagent plume to align over the full width of detection zones as described above.

To maintain a uniform flow front across the width of the detection zone, the inventors determined that the pillar geometry around the corner had to be modified or replaced altogether in order to maintain a uniform flow front in the flow path downstream of the corner section.

Accordingly, one aspect of the invention provides modifying the configuration of the projections in or around the corner section to maintain a uniform flow front downstream of the corner section. As used herein, modifying the configuration of the projections can include replacing the projections in the corner section altogether with other configurations as described in detail below. While any modification that maintains the configuration of the flow front after it exits the corner section as it had before the corner section (preferably uniform) can be used, the following modifications are particularly preferred. Although the description of the corner sections and projection modifications in the description above and below are generally made with reference to the detection zone, the advantages of the invention are application any zone or portion of the fluid flow path in the device using projections.

The corner sections can change the direction of the flow path by any desired amount. Preferably the change in direction is at least 30 degrees and can be up to 270 degrees, and preferably 90 degrees to 180 degrees.

Figure 6:
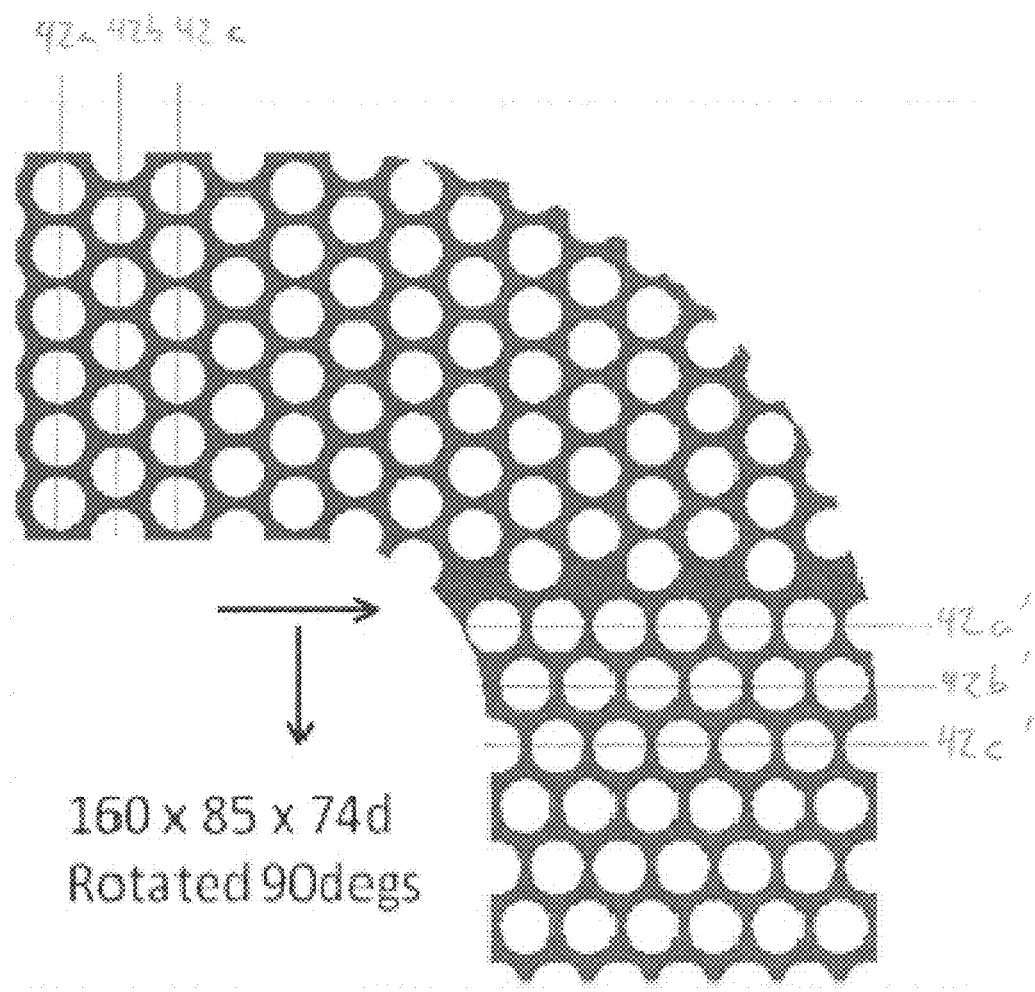
FIG. 6 shows an enlarged schematic view of a corner of a flow path in a detection zone having modified micropillar spacing according to a preferred embodiment of the invention.

According to one preferred embodiment, the projections are rotated before or after the turn to maintain the uniform flow profile after the turn. The amount rotated will depend on the change in the flow of direction. For example a flow path that turns 30° will have the projections rotated approximately 30°, whereas a flow path that turns 90° will have the projection rotated approximately 90°. FIG. 6 shows the pillars rotated after the turn for a 90° change in flow direction. In the FIG. 6 embodiment, the rows 42a, 42b, 42c, etc., before they turn are perpendicular to the direction of flow. As the pillars move into the turn they maintain this configuration. If this configuration continued the rows would be parallel to the direction of fluid flow. Instead, the inventors have found that re-orienting the projections to where they form rows 42a', 42b', 42c', etc., after the turn ensures that the fluid maintains the configuration after the turn.

Figure 7:
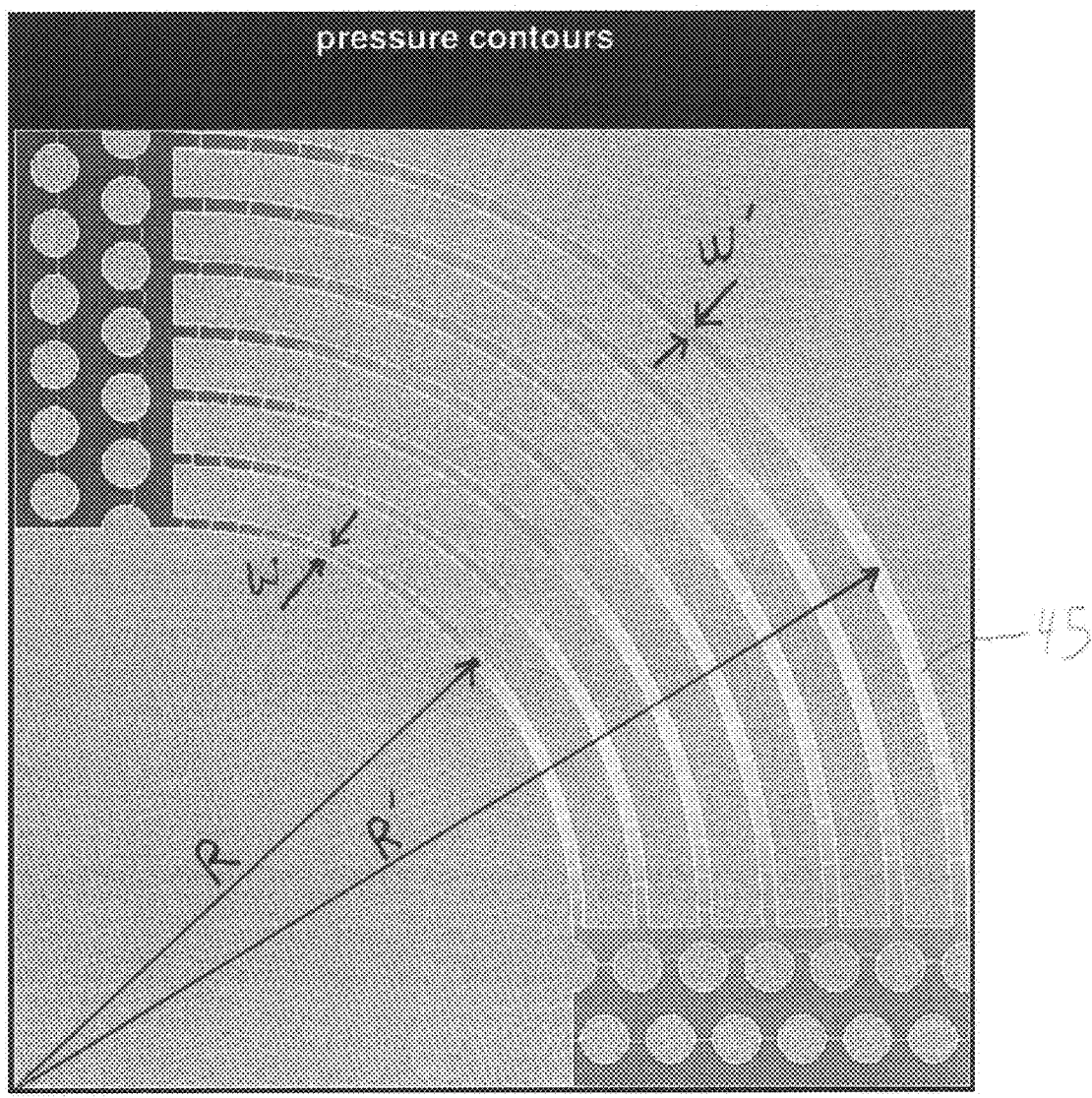
FIG. 7 shows an enlarged schematic view of a corner of a flow path in a detection zone having contoured corner channels according to a preferred embodiment of the invention.

According to another preferred embodiment, to ensure a uniform velocity profile across the width of the channel and the same pressure gradient at the inlet and outlet of the corner section, contoured microchannels 45 without projections can be used at the turns or corners in place of projections as shown in FIG. 7. To obtain the same flow rate for each channel at the same pressure gradient between channel inlets and outlets, the channel cross-sectional area (A) and the mid-line radius (R) should maintain the relationship of $A^2/R$=constant and the distances between neighboring channels remains the same. If the channel height is the same, then the microchannel width (W) and the mid-line radius (R) of the flow channel should maintain the relationship $W^2/R$=constant. By modifying the widths of the microchannels, the flow rate across the channel is the same and the flow rate at the inlet and outlet will be the same as long as the distance between each microchannel is the same and the channel heights are the same. The relationship between W and R is shown in FIG. 7. The radius of the innermost flow channel is shown as R and the width as W, whereas the radius of the outermost flow channels is shown as R' and the width as W'. To achieve the same flow rate at the inlet and outlet of the channels and hence a uniform flow front after the corner section the condition $W^2/R=W'^2/R'$ must be meet. The smallest microchannel width can range from 5 μm to 30 μm. and preferably from 10 μm to 30 μm.

The corner sections can change the direction of the flow path by any desired amount. Preferably the change in direction is at least 30 degrees and can be up to 270 degrees, and preferably 90 degrees to 180 degrees.

Downstream from the detection zone is a wicking zone in fluid communication with the detection zone. The wicking zone is an area of the assay device with the capacity of receiving liquid sample and any other material in the flow path, e.g., unbound reagents, wash fluids, etc. The wicking zone provides a capillary force to continue moving the liquid sample through and out of the detection zone. The wicking zone can include a porous material such as nitrocellulose or can be a non-porous structure such as the projections described herein. The wicking zone can also include non-capillary fluid driving means, such as using evaporative heating or a pump. Further details of wicking zones as used in assay devices according to the present invention can be found in patent publications US 2005/0042766 and US 2006/0239859, both of which are incorporated herein by reference in their entireties. Wicking zones are also described in copending patent application entitled "Controlling Fluid Flow Through An Assay Device" (Application No. 61/588,772, first named inventor: James Kanaley), filed Jan. 20, 2012 and incorporated by reference in its entirety.

Preferably the entirety of the flow path including the sample addition zone, the detection zone and the wicking zone includes projections substantially vertical in relation to the substrate, and having a height, diameter and reciprocal spacing capable of creating lateral flow of the sample in the flow path.

In any of the above embodiments, the device is preferably a disposable assay device. The assay device may be contained in a housing for ease of handling and protection. If the assay device is contained in such a housing, the housing will preferably include a port for adding sample to the assay device.

The assay device of the present invention can be used with a device for reading (a reader) the result of an assay device performed on the assay of the present invention. The reader includes means for reading a signal emitted by, or reflected from the detection element, such as a photodetector, and means for computing the signal and displaying a result, such as microprocessor that may be included within an integrated reader or on a separate computer. Suitable readers are described for example in US 2007/0231883 and U.S. Pat. No. 7,416,700, both of which are incorporated by reference in their entireties.

Another embodiment is a device for reading the result of an assay performed on an assay device, wherein the device comprises a detector capable of reading a signal emitted from or reflected from at least one detection element present in a defined location of the assay device. In either of the above embodiments, the reading preferably is chosen from the detection and/or quantification of color, fluorescence, radioactivity or enzymatic activity.

Another aspect of the invention is directed to a method of performing an assay on a liquid sample for the detection of one or more analytes of interest. A liquid sample containing the analyte(s) of interest is deposited onto the sample addition zone of the assay device, such as through a port in the housing of the device, or by touching off a finger directly onto the sample addition zone in the case of a fingerstick blood draw. The sample moves by capillary action in the fluid flow path through an optional filter, and into the reagent zone where it dissolves the one or more reagents. The sample flows away from the reagent zone and optionally the reagent addition zone having a dissolved reagent plume and into the detection zone. At some point in the flow path, the flow will encounter a corner section, the uniform flow front of the sample and hence the width of the reagent plume is maintained by the modifications of the projections before, in or after the corner section according to the present invention.

Next the sample moves by capillary action into the detection zone. In the detection zone, a signal representative of an analyte or control is produced. In a preferred embodiment the sample or the one or more reagents having a detection element is captured in the detection zone, such as by antibodies on the surface of the detection zone and a signal representative of the presence or concentration of the analyte(s) or control(s) is produced. The reader or detection instrument as described above is then used to read the signal that is produced in the detection zone to determine the presence or concentration of the analyte(s) or control(s). The sample moves from the detection zone and into the wicking zone. The reader may read the signal immediately or a short time after the sample has moved through the detection zone. Also, one or more washes may follow the sample through the device to wash any unbound reagents, such as detection element, away from the detection zone.

Another aspect of the invention is a method of controlling the flow of a liquid around the corner section of a fluid flow path an assay device, which includes providing an assay device as described herein. The sample zone, the reagent zone, the detection zone and the wicking zone define a fluid flow path and at least a part of the fluid flow path has a substrate and projections which extend substantially vertically from the substrate. The projections have a height, cross-section and a distance between one another that defines a space between the projections capable of generating capillary flow parallel to the substrate surface. At least part of the fluid flow path having projections also has a corner section to change the direction of the flow path. The projections in or around the corner section are modified to maintain the flow front of the sample flowing through the flow path after the corner is substantially the same configuration as before the corner.

Sample, such as whole blood, is added to the sample addition zone. The sample flows from the sample addition through the reagent zone into and through the detection zone and into the wicking zone. The sample encounters a corner section where the modifications to the projections maintain the configuration of the flow front of the sample before and after the corner.

The method, assay device, and reader according to an embodiment of the invention have many advantages, mainly related to the improved reaction kinetics of the immunochemical reactions and the increased sensitivity of the assay.

It is to be understood that this invention is not limited to the particular embodiments shown here. The following examples are provided for illustrative purposes and are not intended to limit the scope of the invention since the scope of the present invention is limited only by the appended claims and equivalents thereof.

EXAMPLES

Figure 8:
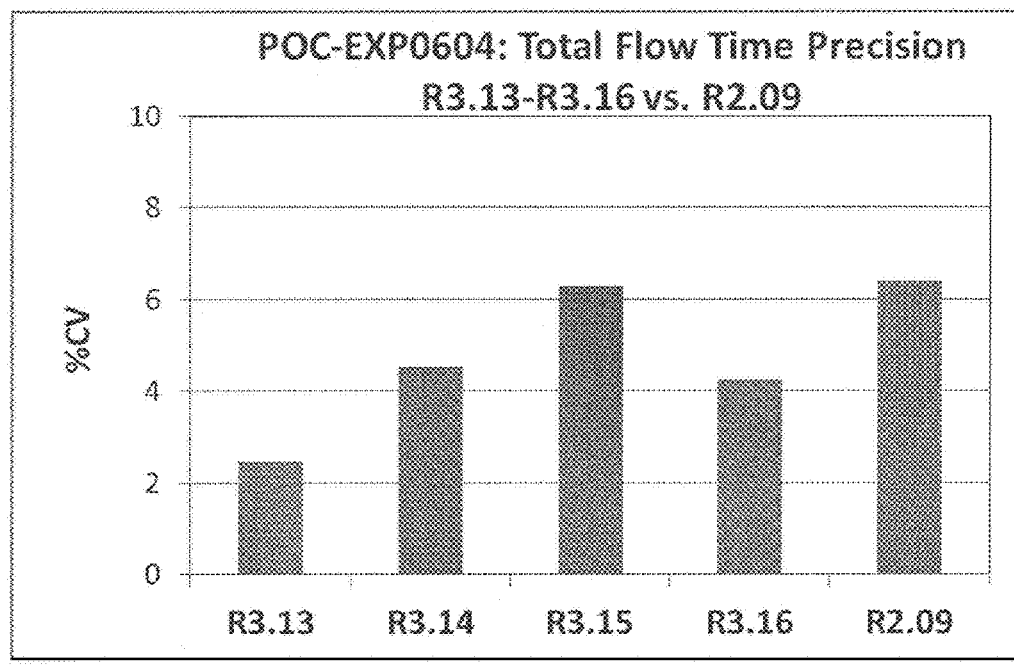
FIG. 8 shows experimental flow time results for assay devices with corners in the flow path compared to a device without corners.
Figure 9:
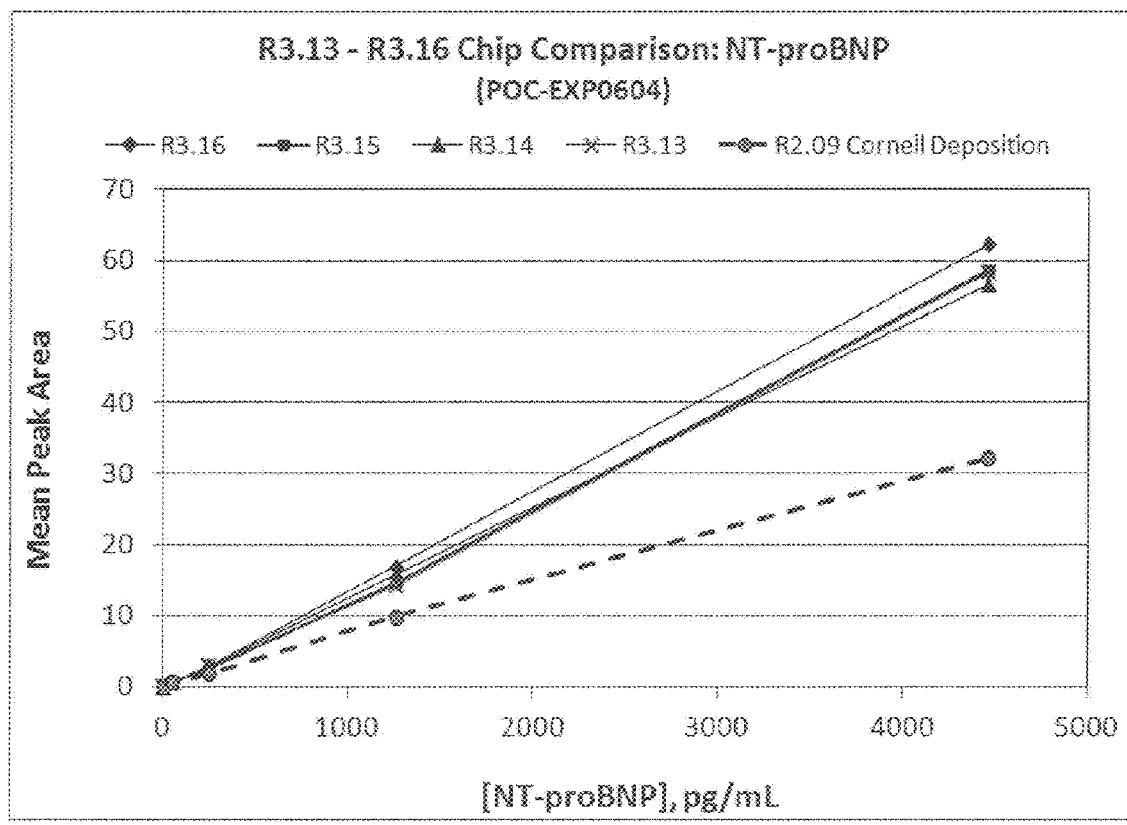
FIG. 9 shows dose-response plots for assay devices with corners in the flow path compared to a device without corners.

Plastic substrate chips made of Zeonor (Zeon, Japan) having oxidized dextran on the surface for covalent immobilization of proteins via Schiff base coupling were used. Fluorescently labeled Anti-NT-proBNP monoclonal antibody was deposited and dried to create a reagent zone. Anti-NT-proBNP monoclonal antibody was deposited and dried to create a detection zone. A small amount of Triton X-45 was deposited on the device to increase wettability of the sample for better capillary flow. Sample was added to the sample zone of the device and the capillary action of the micropillar array distributed the sample through the flow channel into the wicking zone. A typical assay time was about 10 minutes. The signal intensities from the fluorescently labeled complexes in the detection zone were recorded in a prototype line-illuminating fluorescence scanner. The results from the experiments are shown in FIGS. 8 and 9, which have been described above. The experimental data shown in FIGS. 8 and 9 was collected using serum samples spiked with varying levels of NT-proBNP. In FIGS. 8 and 9, the devices designated as R3.13 and R3.14 have corners in the flow path using the preferred embodiment of the invention shown in FIG. 6. Devices designated as R3.15 and R3.16 have corners in the flow path using the preferred embodiment of the invention shown in FIG. 7. FIG. 8 shows that the variability in total flow times for the devices with corners compared to device R2.09 with a linear flow path is comparable or better. FIG. 9 shows that a good dose-response curve is obtained with the designs that have flow path corners.

Figure 10:
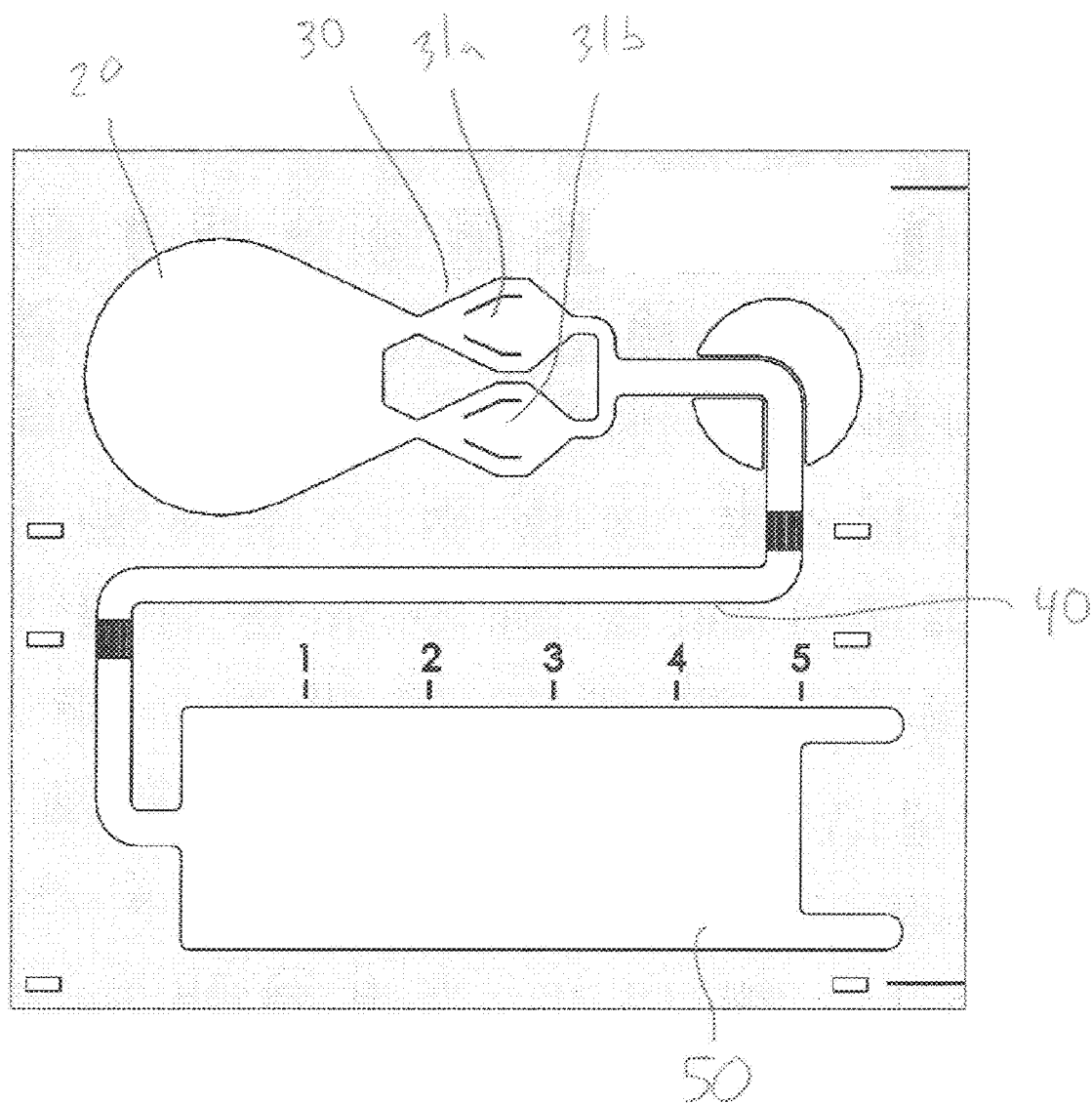
FIG. 10 shows a schematic view of an assay device having corners in the flow path according to another embodiment of the invention.

FIG. 10 shows another embodiment of an assay device having two reagent cells 31a and 31b in the reagent zone 30. A reagent plume will flow from each of these cells and be distinct plumes for at least a portion of the subsequent detection zone 40.

Figure 11:
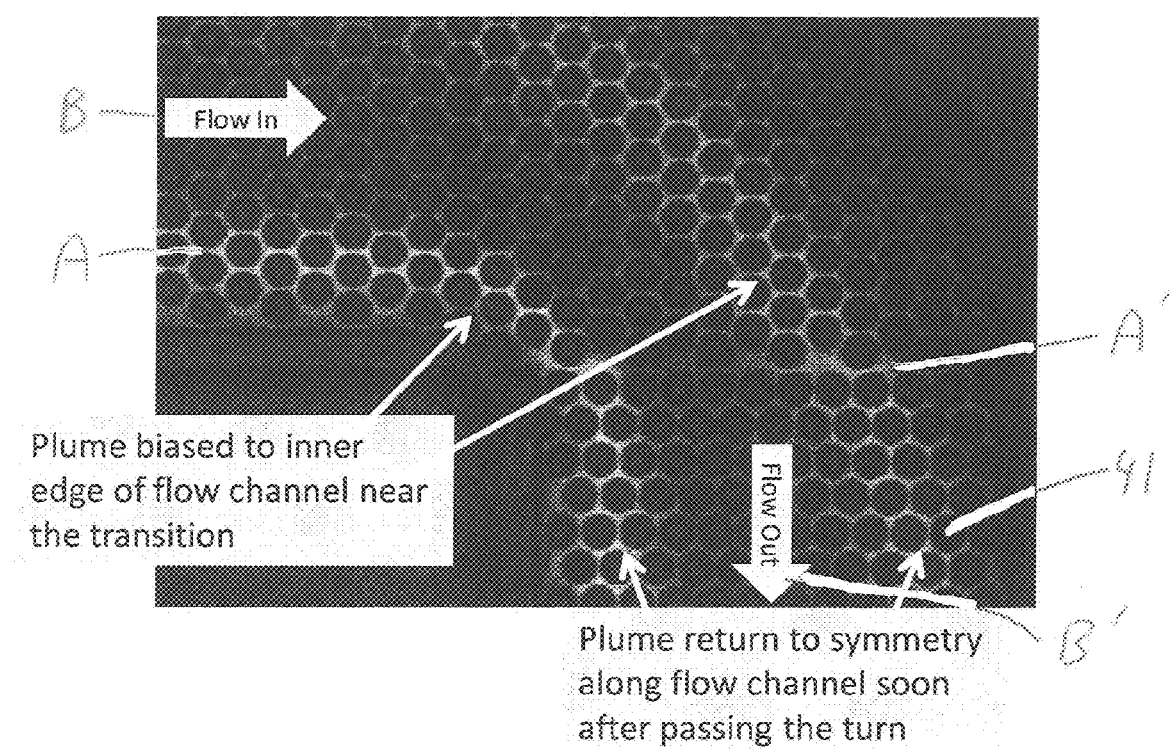
FIG. 11 is a photograph showing the flow of a twin reagent plume around the corner section of the fluid flow path according to one embodiment of the invention.

FIG. 11 shows a photograph showing flow around the corner according to one embodiment of the invention where the projections are rotated after the turn. In FIG. 11, the direction of flow is shown by arrows B and B'. The light colored shading shown as A and A' are distinct reagent plumes coming from reagent cells 31a and 31b before they have combined to form a single wide plume. As shown in FIG. 11 the plumes are biased toward the inner edge of the flow channel as they round the corner. However, as the figure shows, the plumes return to substantially the same symmetry after completing the turn.

Figure 12:
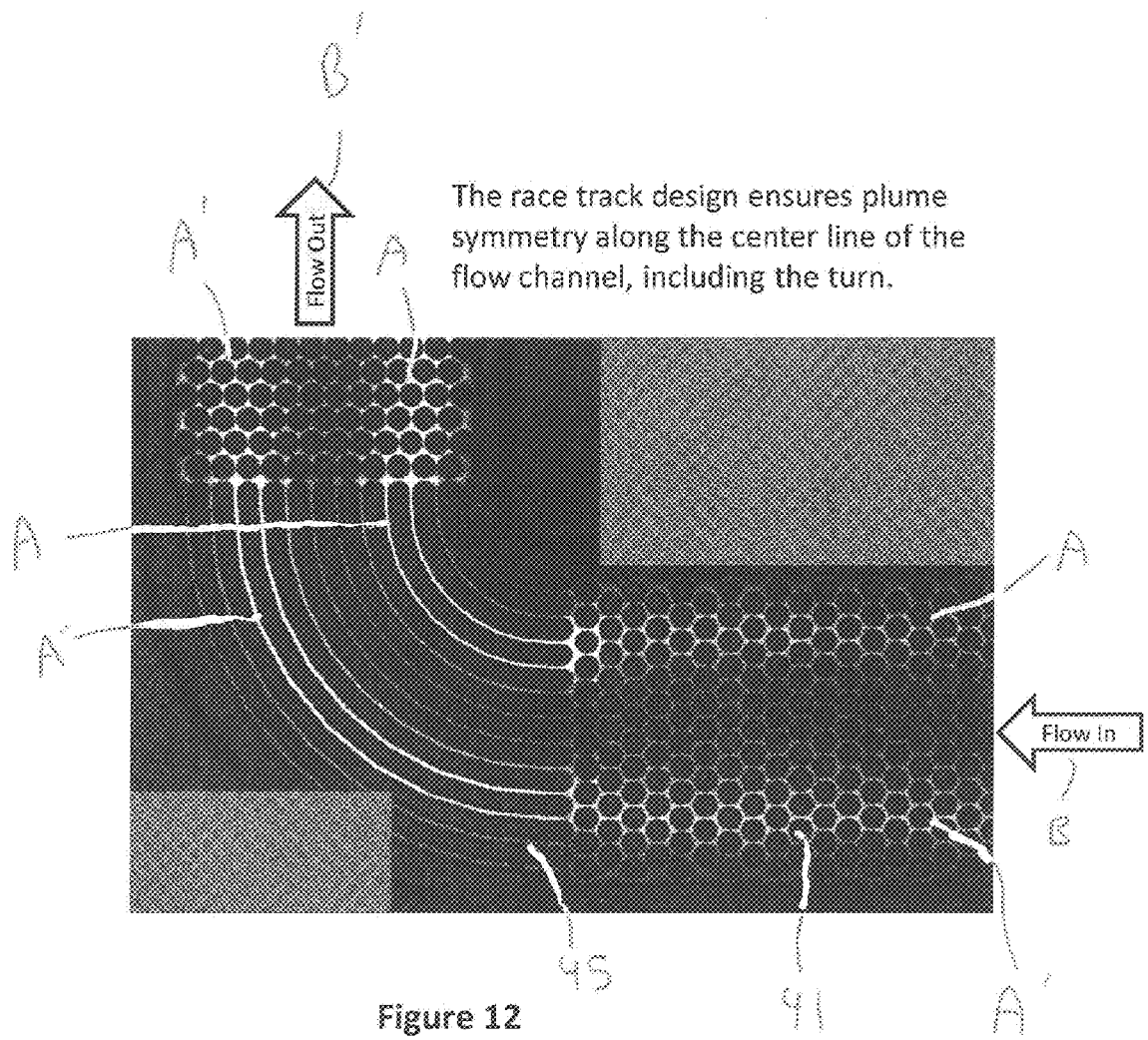
FIG. 12 is a photograph showing the flow of a twin reagent plume around the corner section of the fluid flow path according to one embodiment of the invention.

FIG. 12 shows a photograph showing flow around the corner according to one embodiment of the invention where contoured microchannels 45 are used at the corners instead of projections. In FIG. 12, the direction of flow is shown by arrows B and B'. The light colored shading shown as A and A' are distinct reagent plumes coming from reagent cells 31a and 31b before they have combined to form a single wide plume. As shown in FIG. 12, the plumes retain substantially the same symmetry before, during and after the turn.

Those skilled in the art will appreciate that the invention and embodiments thereof described herein are susceptible to variations and modifications other than those specifically described. It is to be understood that the invention includes all such variations and modifications. The invention also includes all of the steps and features referred to in this specification, individually or collectively, and any and all combinations of any two or more of the steps or features.

Additional Embodiments

1. An assay device comprising: a liquid sample zone; a reagent zone downstream and in fluid communication with the sample zone containing a reagent material; a detection zone in fluid communication with the reagent zone having capture elements bound thereto; and a wicking zone in fluid communication with the capture zone having a capacity to receive liquid sample flowing from the detection zone, wherein the sample receiving zone, the reagent zone, the detection zone and the wicking zone define a fluid flow path and at least a part of the fluid flow path has a substrate and projections which extend substantially vertically from the substrate, wherein the projections have a height, cross-section and a distance between one another that defines a space between the projections capable of generating capillary flow parallel to the substrate surface, wherein the fluid flow path having projections includes a corner section which changes the direction of the flow path, and wherein the projections in or around the corner section are modified to maintain the configuration of the flow front of the sample flowing through the flow path after the corner is substantially the same configuration as before the corner.

2. An assay device as described in embodiment 1, wherein the reagent zone comprises a labeled conjugate material.

3. An assay device as described in embodiment 1, wherein the detection zone comprises zone capture elements bound thereto.

4. An assay device as described in embodiment 1, further comprising a filter after the sample zone, and a reaction addition zone located before or after the reagent zone.

5. An assay device as described in embodiment 1, wherein the direction of the flow path is changed at least 30°.

6. An assay device as described in embodiment 1, wherein the direction of the flow path is changed as much as 270°.

7. An assay device as described in embodiment 1, wherein the modification of the projections comprises replacing the projections in the corner section with a plurality of microchannels.

8. An assay device as described in embodiment 7, wherein each of the microchannels have a radius of R and a cross-sectional area of A, and the microchannels satisfy the relationship $A^2/R$=constant.

9. An assay device as described in embodiment 8, wherein the channel height is a constant and $W^2/R$=constant, where W is the width of the microchannel.

10. An assay device as described in embodiment 1, wherein the modification of the projections comprises altering the arrangement of at least some of the projections in or around the corner section.

11. An assay device as described in embodiment 10, wherein the pattern of the at least some of the projections is rotated in the range of about 30 to 270° depending on the change in direction of the flow path.

12. An assay device as described in embodiment 11, wherein the pattern is rotated immediately before or after the corner.

13. An assay device as described in embodiment 1, wherein total area of the assay device is $\leq 900$ mm$^2$.

14. An assay device as described in embodiment 13, wherein total area of the assay device is $\leq 700$ mm$^2$.

15. An assay device as described in embodiment 1, wherein the assay device is rectangular and the dimensions of each side are $\leq 30$ mm.

16. An assay device as described in embodiment 15, wherein the assay device is rectangular and the dimensions are approximately $\leq 24\times 28$ mm.

17. An assay device as described in embodiment 1, wherein the assay device is capable of using a sample size of $\leq 50$ μl.

18. An assay device as described in embodiment 17, wherein the assay device is capable of using a sample size of $\leq 40$ μl.

19. An assay device as described in embodiment 18, wherein the assay device is capable of using a sample size of $\leq 35$ μl.

20. An assay device as described in embodiment 19, wherein the assay device is capable of using a sample size of $\leq 25$ μl.

21. A method of controlling the flow of a liquid around the corner section of a fluid flow path in an assay device comprising: providing a liquid sample zone;

providing a reagent zone downstream and in fluid communication with the sample addition zone containing a reagent material; providing a detection zone in fluid communication with the reagent zone; providing a wicking zone in fluid communication with the detection zone having a capacity to receive liquid sample flowing from the detection zone, wherein the sample receiving zone, the reagent zone, the detection zone and the wicking zone define a fluid flow path and at least a part of the fluid flow path has a substrate and projections which extend substantially vertically from the substrate, wherein the projections have a height, cross-section and a distance between one another that defines a space between the projections capable of generating capillary flow parallel to the substrate surface, and wherein the at least part of the fluid flow path having projections has a corner section to change the direction of the flow path, wherein the projections in or around the corner section are modified to maintain the flow front of the sample flowing through the flow path after the corner is substantially the same configuration as before the corner; adding sample to the sample addition zone; flowing the sample from the sample addition through the reagent zone into and through the detection zone and into the wicking zone, wherein the sample encounters at least one corner section, anywhere in the flow path and wherein the modifications to the projections maintain the configuration of the flow front of the sample before and after the corner.

22. A method as described in embodiment 21, wherein the direction of the flow path is changed at least 30°.

23. A method as described in embodiment 21, wherein the direction of the flow path is changed as much as 270°.

24. A method as described in embodiment 21, wherein the modification of the projections comprises replacing the projections in the corner section with a plurality of microchannels.

25. A method as described in embodiment 14, wherein each of the microchannels have a radius of R and a cross-sectional area of A, and the microchannels satisfy the relationship $A^2/R=$constant.

26. A method as described in embodiment 21, wherein the modification of the projections comprises altering the arrangement of at least some of the projections in or around the corner section.

27. A method as described in embodiment 26, wherein the pattern of the at least some of the projections is rotated in the range of about 30 to 270° depending on the change in direction of the flow path.

28. A method as described in embodiment 27, wherein the pattern is rotated immediately before or after the corner.

29. A method as described in embodiment 21, wherein the corner section is in the detection zone.

30. A method of performing an assay on a liquid sample for the detection of one or more analytes of interest, comprising: providing a liquid sample zone; providing a reagent zone downstream and in fluid communication with the sample addition zone containing a reagent material; providing a detection zone in fluid communication with the reagent zone; providing a wicking zone in fluid communication with the detection zone having a capacity to receive liquid sample flowing from the detection zone, wherein the sample receiving zone, the reagent zone, the detection zone and the wicking zone define a fluid flow path and at least a part of the fluid flow path has a substrate and projections which extend substantially vertically from the substrate, wherein the projections have a height, cross-section and a distance between one another that defines a space between the projections capable of generating capillary flow parallel to the substrate surface, and wherein the at least part of the fluid flow path having projections has a corner section to change the direction of the flow path, wherein the projections in or around the corner section are modified to maintain the flow front of the sample flowing through the flow path after the corner is substantially the same configuration as before the corner; depositing a liquid sample containing the analyte(s) of interest onto the sample zone; moving the sample by capillary action into the reagent zone where it dissolves the reagent material; flowing the sample away from the reagent zone having a dissolved reagent plume and into a detection zone by capillary action, where the analytes are detection by reading a signal that is generated to determine the presence or concentration of the analyte(s); and flowing the sample and any other unbound material into the wicking zone.

31. A method as described in embodiment 30, wherein the sample moves from the detection zone and into the wicking zone, and the signal may be read immediately or a short time after the sample has moved through the detection zone.

32. A method as described in embodiment 30, wherein one or more washes may follow the sample through the assay device to wash any unbound detection element away from the detection zone.

33. A method as described in embodiment 30, wherein the reagent material is conjugated material conjugated with a detection element, and the reagent plume is a conjugate plume.

34. A method as described in embodiment 30, where the detection zone contains capture elements to capture the detection element.

35. A method as described in embodiment 34, wherein the signal is generated by the detection element.

36. A method as described in embodiment 30, wherein total area of the assay device is $\leq 900$ mm$^2$.

37. A method as described in embodiment 36, wherein total area of the assay device is $\leq 700$ mm$^2$.

38. A method as described in embodiment 30, wherein the assay device is rectangular and the dimensions of each side are $\leq 30$ mm.

39. A method as described in embodiment 38, wherein the assay device is rectangular and the dimensions are approximately $\leq 24 \times 28$ mm.

40. A method as described in embodiment 1, wherein the sample size is $\leq 50$ µl.

41. A method as described in embodiment 40, wherein the sample size is $\leq 40$ µl.

42. A method as described in embodiment 41, wherein the sample size is $\leq 35$ µl.

43. A method as described in embodiment 42, wherein the sample size is $\leq 25$ µl.

Copending applications entitled "Low Volume Assay Device Having Increased Sensitivity" (Application No. 61/588,758, first named inventor: Phil Hosimer), "Assay Device Having Multiplexing" (Application No. 61/588,779, first named inventor: Sue Danielson), "Assay Device Having Multiple Reagent Cells" (Ser. No. 61/588,738, first named inventor Zhong Ding), "Controlling Fluid Flow Through An Assay Device" (Application No. 61/588,772, first named inventor James Kanaley), and "Assay Device Having Controllable Sample Size" (Application No. 61/588,899, first named inventor, Ed Scalice), all filed Jan. 20, 2012 and all incorporated by reference in their entireties.

What is claimed is:

1. An assay device comprising:
    a liquid sample zone;
    a reagent zone downstream and in fluid communication with the sample zone containing a reagent material;
    a detection zone in fluid communication with the reagent zone having capture elements bound thereto; and
    a wicking zone in fluid communication with the capture zone having a capacity to receive liquid sample flowing from the detection zone,
    wherein the sample receiving zone, the reagent zone, the detection zone and the wicking zone define a fluid flow path and at least a part of the fluid flow path has a substrate and projections which extend substantially vertically from the substrate, wherein the projections have a height, cross-section and a distance between one another that defines a space between the projections capable of generating capillary flow parallel to the substrate surface,
    wherein the fluid flow path having projections includes a corner section which changes the direction of the flow path, and wherein the projections in or around the corner section are modified to maintain the configuration of the flow front of the sample flowing through the flow path after the corner is substantially the same configuration as before the corner, and wherein the modification of the projections comprises replacing the projections in the corner section with a plurality of microchannels.

2. An assay device as claimed in claim 1, wherein the reagent zone comprises a labeled conjugate material.

3. An assay device as claimed in claim 1, wherein the detection zone comprises zone capture elements bound thereto.

4. An assay device as claimed in claim 1, wherein the direction of the flow path is changed at least 30°.

5. An assay device as claimed in claim 1, wherein each of the microchannels have a radius of R and a cross-sectional area of A, and the microchannels satisfy the relationship $A^2/R$=constant.

6. An assay device as claimed in claim 5, wherein the channel height is a constant and $W^2/R$=constant, where W is the width of the microchannel.

7. An assay device as claimed in claim 1, wherein the assay device is capable of using a sample size of ≤50 µl.

8. A method of controlling the flow of a liquid around the corner section of a fluid flow path in an assay device comprising:
provide an assay device as claimed in claim 1;
adding sample to the liquid sample azone;
flowing the sample from the sample addition through the reagent zone into and through the detection zone and into the wicking zone, wherein the sample encounters the corner section, and
wherein the modifications to the projections maintain the configuration of the flow front of the sample before and after the corner.

9. A method as claimed in claim 8, wherein the direction of the flow path is changed at least 30°.

10. A method as claimed in claim 8, wherein the direction of the flow path is changed as much as 270°.

11. A method as claimed in claim 8, wherein each of the microchannels have a radius of R and a cross-sectional area of A, and the microchannels satisfy the relationship $A^2/R$=constant.

12. A method as claimed in claim 8, wherein the corner section is in the detection zone.

13. A method of performing an assay on a liquid sample for the detection of one or more analytes of interest, comprising:
providing an assay device as claimed in claim 1;
depositing a liquid sample containing the analyte(s) of interest onto the liquid sample zone;
moving the sample by capillary action into the reagent zone where it dissolves the reagent material;
flowing the sample away from the reagent zone having a dissolved reagent plume and into a detection zone by capillary action, where the analytes are detection by reading a signal that is generated to determine the presence or concentration of the analyte(s); and
flowing the sample and any other unbound material into the wicking zone.

14. A method as claimed in claim 13, wherein the sample size is ≤50 µl.

* * * * *